United States Patent
Cray et al.

(10) Patent No.: US 8,134,887 B1
(45) Date of Patent: Mar. 13, 2012

(54) DIRECTIONAL ACOUSTIC DENSITY SENSOR

(75) Inventors: Benjamin A. Cray, West Kingston, RI (US); Dimitri Donskoy, Hoboken, NJ (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 72 days.

(21) Appl. No.: 12/880,384

(22) Filed: Sep. 13, 2010

(51) Int. Cl.
*G01S 15/58* (2006.01)
(52) U.S. Cl. .......................................................... 367/89
(58) Field of Classification Search .................... 367/89, 367/149
See application file for complete search history.

(56) References Cited

U.S. PATENT DOCUMENTS

| | | | |
|---|---|---|---|
| 5,442,594 A * | 8/1995 | Cray | 367/162 |
| 6,697,302 B1 * | 2/2004 | Cray et al. | 367/141 |

* cited by examiner

*Primary Examiner* — Daniel Pihulic
(74) *Attorney, Agent, or Firm* — James M. Kasischke; Jean-Paul A. Nasser; Michael P. Stanley

(57) ABSTRACT

The invention as disclosed is a fiber optic interferometric directional acoustic density sensor that increases the directionality of a vector sensor that is much smaller in size than the wave length of an acoustic wave. This is accomplished through the use of second order directionality by measuring the acoustic fluctuations of fluid density at a point, wherein the acoustic density fluctuations are determined according to the principles of fluid compressibility and conservation of mass using a density fluctuation measuring apparatus that restricts two of the three vector components of the particle velocity of the acoustic wave and that employs a laser interferometer to measure the fluid density fluctuation along the remaining vector component.

3 Claims, 1 Drawing Sheet

DIRECTIONAL ACOUSTIC DENSITY SENSOR

STATEMENT OF GOVERNMENT INTEREST

The invention described herein may be manufactured and used by or for the Government of the United States of America for governmental purposes without the payment of any royalties thereon or therefore.

CROSS REFERENCES TO OTHER PATENT APPLICATIONS

None.

BACKGROUND OF THE INVENTION (1) Field of the Invention

The present invention is directed to acoustic vector sensors. In particular, the present invention is directed to increasing the directionality of a sensor having a size much less than the wave length of an acoustic wave, by measuring the acoustic fluctuations of fluid density at a point.

(2) Description of the Prior Art

Conventional vector sensors measure particle velocity, v ($v_x$, $v_y$, $v_z$), associated with an acoustic wave. The measurements of a vector quantity (velocity) instead of a scalar quantity (pressure) allows for directional sensing even if the size of the vector sensor is much smaller than the size of the wavelength of the acoustic wave. The directionality pattern of a vector sensor is proportional to $\cos(\theta)$, where $\theta$ is the directional angle of the vector sensor. Vector sensor directionality is equivalent to the dipole-type or first order sensor that is realized by measuring particle velocity at a point, (which is the vector sensor sensing approach for underwater sensors), or by measuring the gradient of the acoustic pressure at two closely spaced (less than the wavelength of an acoustic wave) points as it is commonly done in air acoustics where this type of sensor is called an acoustic intensity probe. The two approaches of obtaining vector sensor directionality as described above are in fact mathematically equivalent according to a linearized equation of momentum conservation as expressed in Eq. (1) below:

$$\rho_0 = \frac{\partial v}{\partial t} + \nabla p = 0 \tag{1}$$

Here $\rho_0$ is the undisturbed fluid density and is the $\nabla p$ gradient of the acoustic pressure. For a plane wave propagating in the x-direction Eq. (1) can be re-written as Eq. (2) below:

$$\rho_0 \frac{\partial v}{\partial t} = -\frac{\partial p}{\partial x} \tag{2}$$

There continues to be a need to increase the directionality of a vector sensor. One approach to further increase the directionality of a vector sensor while still maintaining a sensor size that is much smaller than the wavelength of an acoustic wave, is to utilize a second order or quadruple-type sensor arrangement measuring the diversion of the velocity, div v. This can be accomplished by measuring the components of the velocity, v ($v_x$, $v_y$, $v_z$), at closely spaced points (at least two points) along the corresponding axis yielding the directionality, which is proportional to $\cos^2(\theta)$. The benefit of the increased directionality, however, when measured using this approach comes at a cost of the number of vector sensors necessary and at a cost of a reduction in sensitivity. Two vector sensors for each axis (a minimum of six sensors) are required to measure the diversion of the velocity and there is a significant reduction in sensor sensitivity proportional to kd<<1, where k is the wave-number and d is the spacing between the two vector sensors.

A more advantageous means to achieve a second order directionality is to measure the acoustic fluctuations of fluid density at a point rather than directly measuring the diversion of the velocity.

SUMMARY OF THE INVENTION

It is a general purpose and object of the present invention to increase the directionality of a vector sensor having a size much less than the wave length of an acoustic wave.

The above object is accomplished with the present invention through the use of second order directionality by measuring the acoustic fluctuations of fluid density at a point, wherein the acoustic density fluctuations are determined according to the principles of fluid compressibility and conservation of mass using a density fluctuation measuring apparatus that restricts two of the three vector components of the particle velocity of the acoustic wave and that employs a laser interferometer to measure the fluid density fluctuation along the remaining vector component.

BRIEF DESCRIPTION OF THE DRAWINGS

A more complete understanding of the invention and many of the attendant advantages thereto will be more readily appreciated by referring to the following detailed description when considered in conjunction with the accompanying drawings, wherein like reference numerals refer to like parts and wherein.

DETAILED DESCRIPTION OF THE INVENTION

Acoustic density fluctuations are determined by fluid compressibility and conservation of mass and are respectively described by the following two linearized equations:

$$\frac{\rho}{\rho_0} = \frac{1}{B} p \tag{3}$$

and $$\frac{1}{\rho_0} \frac{\partial \rho}{\partial t} = -\frac{\partial v_x}{\partial x} - \frac{\partial v_y}{\partial y} - \frac{\partial v_z}{\partial z} \tag{4}$$

where $\rho = \rho_{total} - \rho_0$ is the density disturbance due to an acoustic wave and B is the fluid bulk modulus. Equation (4), above, provides the basis for a second order vector sensor utilizing density acoustic fluctuation measurements provided that the measured fluctuations are only associated with one component of $$div \vec{v} = \frac{\partial v_x}{\partial x} + \frac{\partial v_y}{\partial y} + \frac{\partial v_z}{\partial z}$$

(i.e., the right hand side of Equation (4)). This is achieved by using a measuring cell 10 that restricts two of the spatial vector components of particle velocity associated with the acoustic wave. Such a measuring cell 10 is illustrated in the FIG. 1.

Figure 1:
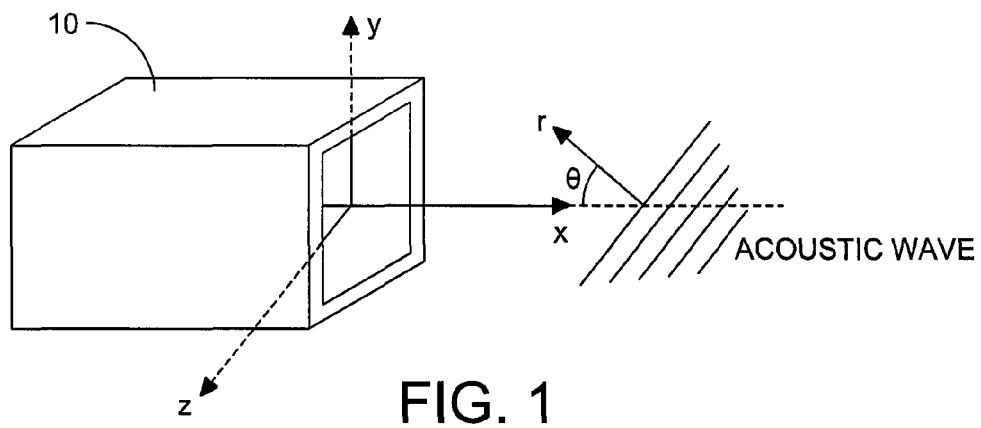
FIG. 1 illustrates a measuring cell that restricts two of the three vector components of velocity.

In the measuring cell 10 illustrated in FIG. 1, the fluid flow is restricted in y and z directions, while fluid flow is permitted along the x axis. Correspondingly, in terms of the fluid flow within this cell:

$$\frac{\partial v_y}{\partial y} = \frac{\partial v_z}{\partial z} = 0,$$

leaving Eq. (4) in a form similar to Eq. (2) and similarly forming the basis for a new (second order) vector sensor equation:

$$\frac{1}{\rho_0}\frac{\partial \rho}{\partial t} = -\frac{\partial v_x}{\partial x} \quad (5)$$

Taking the time derivative of the Eq. (3) and combining it with Eq. (5) yields the equation for the total density fluctuations:

$$\frac{\partial \rho}{\partial t} = \frac{\rho_0}{2B}\frac{\partial p}{\partial t} - \frac{\rho_0}{2}\frac{\partial v_x}{\partial x} \quad (6)$$

For a plane harmonic wave propagating along an arbitrary direction, r:

$$p = P_0 e^{j(\omega t - \vec{k}\cdot\vec{r})}, \text{ and } v_x = \frac{P_0}{\rho_0 c_0}\cos\theta\, e^{j(\omega t - kx\cos\theta)}, \quad (7)$$

where $P_0$ is the acoustic pressure amplitude, $c_0 = \sqrt{(B/\rho_0)}$ is the speed of the acoustic wave in fluid, $\omega$ is angular frequency of the acoustic plane-wave, t is unit of time, vector k is the acoustic wave-vector, vector r is the positional vector in the Cartesian coordinates of the reference frame, x is the spatial coordinate along the x-axis, and j is the square root of negative one.

Substituting Eq. (7) into Eq. (6) a solution for the total density fluctuation is obtained:

$$|\rho| = \frac{P_0}{2c_0^2} + \frac{P_0}{2c_0^2}\cos^2\theta \quad (8)$$

Here the first and second terms on the right hand side of Eq. (8) are determined by the Eq. (3) and (5), respectively.

In order to achieve a desirable second order directionality while preserving the high sensitivity of the measurements the directly measured density fluctuation is determined by only the second term in Eq. (8):

$$\frac{P_0}{2c_0^2}\cos^2(\theta).$$

In a preferred embodiment an optical interferometer scheme is implemented to directly measure the density fluctuation.

Figure 2:
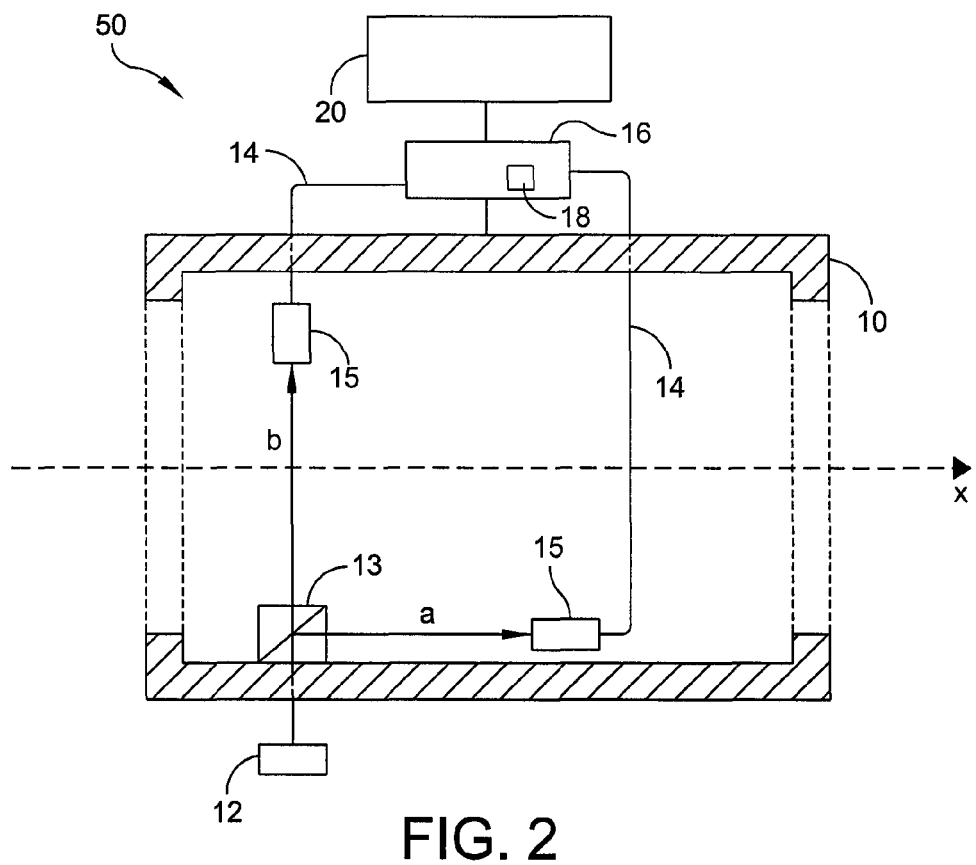
FIG. 2 illustrates a density fluctuation measuring apparatus that employs a laser interferometer.

An example of the optical interferometer apparatus 50 of the present invention is illustrated in the FIG. 2. In a preferred embodiment there is a measuring cell 10 (the measuring cell 10 is rectangular, as previously illustrated in FIG. 1) with acoustically rigid walls (i.e., the walls do not move or flex in any way due to the incident acoustic wave). Measuring cell 10 is filled with water or another fluid medium. In an alternative embodiment the measuring cell 10 has a circular cross-section. Inside of measuring cell 10 there are two laser beams a and b that originate from the same coherent optical light source 12. The light from light source 12 is split with beam splitter 13 into two perpendicular beams: beam a is along the cell axis x (measuring beam) and beam b, perpendicular to the axis x (reference beam). The in-fluid lengths of both beams are equal. Both beams are collected into one end of separate optical fiber cables 14 with beam to fiber couplers 15 at the ends of the cables 14 that collect the beams. The optical fiber cables 14 are connected at their other end to a mixing cell 16 that is equipped with a photodiode 18. The two laser beams a and b are mixed in a mixing cell 16. The lengths of fibers 14 are tuned to create constructive or destructive interference inside the mixing cell 16. The mixing cell 16 is joined to a data acquisition and digital processing unit 20 that is programmable. Because the light index of refraction, n, is highly sensitive to the density fluctuations of the medium, any difference in density fluctuations along beam a (as opposed to beam b) can be detected by the data acquisition and digital processing unit 20 with high precision.

If the incident acoustic wave travels perpendicular to axis x, that is $\cos(\theta)=0$, the density change along both beams a and b will be the same and determined only by the first (scalar) term of Eq. (8). Consequently, there is no difference in the density fluctuations along the beams. This results in zero output of the interferometer. The maximum difference will be achieved if the acoustic wave travels along axis x, that is, $\cos(\theta)=1$. In this scenario, the density change along beam a will be twice as high as along beam b. For an arbitrary direction of the incident acoustic wave, the change in density will be proportional to the second term in Eq. (8).

The interferometer apparatus 50 will measure phase difference, $\Delta\phi$, between the reference beam b and measuring beam a:

$$\Delta\phi \cong (2\pi/\lambda_{light})L(\Delta C_{ab}/C_b), \quad (9)$$

where $\lambda_{light}$ is the light wavelength in the fluid, L is the length of the either beam in the fluid, $C_b$ is the speed of light in the fluid along beam b, $\Delta C_{ab}=C_a-C_b$ is the difference in speeds of lights along beams a and b determined by the difference in the refraction indexes, $n_a$ and $n_b$, along the respective beams:

$$\Delta C_{a,b} = C_V/n_{a,b} \quad (10)$$

The density dependence of the refraction index for light in water is determined by the following formula, (assuming $\rho/\rho_0 \ll 1$, here $\rho$ is the acoustic density disturbance);

$$\frac{n^2-1}{n^2+2} \cong a_0\left(\frac{\rho}{\rho_0}+1\right) \quad (11)$$

where the index of refraction $n=C_V/C_F$, $C_F$ is the speed of light in the fluid, $C_V \cong 3 \cdot 10^8$ m/s is the speed of light in vacuum, and $a_0$ is a constant determined by temperature, light wavelength, and static pressure. Solving (11) for n:

$$n_{a,b} = \sqrt{\frac{2a_0 + 1 + 2a_0(\rho_{a,b}/\rho_0)}{1 - a_0 - a_0(\rho_{a,b}/\rho_0)}} \quad (12)$$

Here $\rho_a$ and $\rho_b$ are the acoustic density disturbances along the respective beams a and b. The acoustic density disturbances $\rho_a$ and $\rho_b$ when represented by Eq. (8) yield the following equations:

$$\rho_a = \frac{P_0}{2c_0^2} + \frac{P_0}{2c_0^2}\cos^2\theta \quad (13a)$$

$$\rho_b = \frac{P_0}{2c_0^2} \quad (13b)$$

Taking into account that $\rho_{a,b}/\rho_0 \ll 1$ and using the Taylor's expansion to transform the formulas (12) and (10) we obtain:

$$n_{a,b} = \sqrt{\frac{1+2a_0}{1-a_0}} + \frac{3a_0}{2(1-a_0)^2}\sqrt{\frac{1-a_0}{1+2a_0}}\frac{\rho_{a,b}}{\rho_0} \quad (14)$$

$$\Delta C_{a,b} = C_V \frac{1.5 a_0}{\sqrt{(1-a_0)(1+2a_0)^3}} \frac{P_0}{2\rho_0 c_0^2}\cos^2\theta \quad (15)$$

Expressions (9) and (15) can be used to evaluate the sensitivity of a second order vector sensor of the present invention according to the following equation:

$$P_{0min} = \frac{(1+2a_0)(1-a_0)}{3a_0\pi}\rho_0 c_0^2 \frac{\lambda_{light}}{L}\Delta\varphi_{min} \quad (16)$$

Assuming the following parameters:
interferometer phase measurement accuracy $\Delta\phi_{min}=0.25$ μrad;
L=the beam length ($L_a=L_b=L$) 25.4 mm (1 inch);
$c_0=1500$ m/s, $\rho_0=1000$ kg/m³;
$\lambda_{light}$ (in water)=1 μm (typical for a laser diode);
$a_0=0.202$ (fresh water, 20° C., atm. pressure);
For these parameters and for $\theta=0$ the formula (16) yields sensitivity estimate for the proposed scheme:

$$P_{0\ min} \cong 0.026 \text{ Pa or approximately } SPL \cong 28 \text{ dB re 1 μPa.} \quad (17)$$

The advantage of the present invention is that it is immune to non-acoustic density variations due to temperature and hydrostatic pressure fluctuations as both laser beams (a and b) are equally exposed to these variations.

While it is apparent that the illustrative embodiments of the invention disclosed herein fulfill the objectives of the present invention, it is appreciated that numerous modifications and other embodiments may be devised by those skilled in the art. Additionally, feature(s) and/or element(s) from any embodiment may be used singly or in combination with other embodiment(s). Therefore, it will be understood that the appended claims are intended to cover all such modifications and embodiments, which would come within the spirit and scope of the present invention.

What is claimed is:

1. A directional acoustic density sensor for sensing acoustic waves comprising:
    a measuring cell with acoustically rigid walls that enclose a hollow section within said measuring cell, having apertures at opposite ends of the measuring cell, wherein said measuring cell is filled with a fluid medium, wherein the shape of said measuring cell restricts two of the spatial vector components of a particle velocity associated with the acoustic wave;
    an optical light source joined to said measuring cell and capable of emitting a beam of light in the hollow section within said measuring cell and through said fluid medium;
    a beam splitter joined to a wall within said hollow portion of said measuring cell that is capable of receiving the beam of light that is emitted by the optical light source and splitting said beam of light into a reference beam and a measurement beam, wherein the reference beam is directed perpendicular to the spatial vector component that is not restricted, wherein the measurement beam is directed parallel to the spatial vector component that is not restricted and therefore perpendicular to the reference beam, wherein the in-fluid lengths of both beams are equal;
    a plurality of optical fiber cable having a first end and a second end, said first end housed within the measuring cell and said second end located outside of the measuring cell, wherein the first end of a first optical fiber cable of said plurality of optical fiber cable is capable of receiving the reference beam and the first end of a second optical fiber cable of said plurality of optical fiber cable is capable of receiving the measurement beam at said first end;
    a light mixing cell joined to the second end of the plurality of optical fiber cable for combining the reference beam and the measurement beam, wherein the reference beam and the measurement beam travel along the plurality of optical fiber cable and enter the light mixing cell from the second end of the plurality of optical fiber cable, wherein the fiber lengths of said plurality of optical fiber cable are tuned to create constructive or destructive interference inside the light mixing cell;
    a photodiode joined to and contained in the light mixing cell capable of converting light into current and voltage; and
    a data acquisition and processing module that is programmable joined to said light mixing cell that receives the mixed beam composed of the reference beam and the measurement beam, and is able to detect any differences in fluid density fluctuations of the fluid medium in the measuring cell by measuring the phase difference, $\Delta\phi$, between the reference beam and measuring beam according to the formula $\Delta\phi \cong (2\pi/\lambda_{light})L(\Delta C_{ab}/C_b)$ where $\lambda_{light}$ is the light wavelength in the fluid, L is the length of the either beam in the fluid, $C_b$ is the speed of light in the fluid along the reference beam, $\Delta C_{ab}=C_a-C_b$ is the difference in speeds of lights along the measurement beam and reference beam determined by the difference in the refraction indexes, $n_a$ and $n_b$, along the respective beams according to the formula $C_{a,b}=C_V/n_{a,b}$ where $C_v$ is the speed of light in a vacuum.

2. A method for measuring the acoustic fluctuations of fluid density for the purpose of determining vector sensor second order directionality comprising:

containing a fluid medium in a measuring cell with acoustically rigid walls that enclose a hollow section within said measuring cell, having apertures at opposite ends of the measuring cell;

restricting two of the spatial vector components of a particle velocity associated with an acoustic wave propagating through said contained fluid medium;

emitting a beam of light in the hollow section within said measuring cell through said fluid medium;

splitting said beam of light into a reference beam and a measurement beam, wherein the reference beam is directed perpendicular to the spatial vector component that is not restricted, wherein the measurement beam is directed parallel to the spatial vector component that is not restricted and therefore perpendicular to the reference beam, wherein the in-fluid lengths of both beams are equal;

combining the reference beam and the measurement beam, to create constructive or destructive interference; and detecting any differences in fluid density fluctuations of the fluid medium through the use of a digital processing unit that measures the phase difference, $\Delta\phi$, between the reference beam and the measuring beam to obtain a second order directionality.

3. The method of claim 2 wherein the step of detecting any differences in fluid density fluctuations of the fluid medium further comprises:

measuring a phase difference, $\Delta\phi$, between the reference beam and the measuring beam, wherein the phase difference is represented by $\Delta\phi \cong (2\pi/\lambda_{light})L(\Delta C_{ab}/C_b)$ where $\lambda_{light}$ is the light wavelength in the fluid, L is the length of the either beam in the fluid, $C_b$ is the speed of light in the fluid along the reference beam, $\Delta C_{ab}=C_a-C_b$ is the difference in speeds of lights along the measurement beam and reference beam determined by the difference in the refraction indexes, $n_a$ and $n_b$, along the respective beams according to the formula $C_{a,b}=C_V/n_{a,b}$ where $C_V$ is the speed of light in a vacuum and $$n_{a,b} = \sqrt{\frac{2a_0 + 1 + 2a_0(\rho_{a,b}/\rho_0)}{1 - a_0 - a_0(\rho_{a,b}/\rho_0)}}$$

where $a_0$ is a constant determined by temperature, light wavelength, and static pressure, where $\rho_a$ and $\rho_b$ are the acoustic density disturbances along the respective beams a and b;

determining $\Delta C_{a,b}$ from the measured $\Delta\phi$; and solving for $\cos^2(\theta)$ according to the equation $$\Delta C_{a,b} = C_V \frac{1.5 a_0}{\sqrt{(1-a_0)(1+2a_0)^3}} \frac{P_0}{2\rho_0 c_0^2} \cos^2\theta$$

to obtain a second order directionality along the corresponding axis, wherein said second order directionality is proportional to $\cos^2(\theta)$.

* * * * *